(12) United States Patent
Downey et al.

(10) Patent No.: US 6,206,832 B1
(45) Date of Patent: Mar. 27, 2001

(54) APPARATUS FOR GUIDING MEDICAL INSTRUMENTS DURING ULTRASONOGRAPHIC IMAGING

(75) Inventors: Donal Downey; Aaron Fenster, both of London (CA)

(73) Assignee: Life Imaging Systems (CA)

( * ) Notice: Subject to any disclaimer, the term of this patent is extended or adjusted under 35 U.S.C. 154(b) by 0 days.

(21) Appl. No.: 09/308,384

(22) PCT Filed: Nov. 28, 1997

(86) PCT No.: PCT/CA97/00904

§ 371 Date: Aug. 20, 1999

§ 102(e) Date: Aug. 20, 1999

(87) PCT Pub. No.: WO98/23213

PCT Pub. Date: Jun. 4, 1998

Related U.S. Application Data

(60) Provisional application No. 60/032,058, filed on Nov. 29, 1996.

(51) Int. Cl.[7] ............................................. A61B 8/00
(52) U.S. Cl. ......................... 600/439; 600/562; 600/461; 600/7
(58) Field of Search ................................... 600/437, 439, 600/461, 562, 567, 1, 3, 7, 429, 427; 604/116; 606/130

(56) References Cited

U.S. PATENT DOCUMENTS

| | | | | |
|---|---|---|---|---|
| 5,437,280 | * | 8/1995 | Hossman | 128/653.2 |
| 5,454,371 | | 10/1995 | Fenster et al. . | |
| 5,494,039 | * | 2/1996 | Onik et al. | 128/749 X |
| 5,647,868 | * | 7/1997 | Chinn | 606/21 |
| 5,871,448 | * | 2/1999 | Ellard | 600/459 |
| 5,931,786 | * | 8/1999 | Whitmore, III et al. | 600/459 |
| 5,957,935 | * | 9/1999 | Brown et al. | 606/130 |
| 5,976,092 | * | 11/1999 | Chinn | 600/459 |
| 6,027,446 | * | 2/2000 | Pathak et al. | 600/439 |
| 6,036,632 | * | 3/2000 | Whitmore, III et al. | 600/7 |
| 6,095,975 | * | 8/2000 | Silvern | 600/439 |
| 6,120,493 | * | 9/2000 | Hofmann | 604/506 |
| 6,129,670 | * | 10/2000 | Bordette et al. | 600/427 |

FOREIGN PATENT DOCUMENTS

| | | | |
|---|---|---|---|
| 4010573 | 10/1990 | (DE) | A61B/17/34 |
| 4225001 | 11/1993 | (DE) | A61B/5/055 |
| 96/32066 | 10/1996 | (WO) | A61B/8/14 |

* cited by examiner

*Primary Examiner*—Francis J. Jaworski
(74) *Attorney, Agent, or Firm*—Katten Muchin Zavis

(57) ABSTRACT

A method and apparatus is disclosed, employed in combination with an ultrasonographic system, for assisting in guiding and placing at least one medical instrument into a target tissue during a minimally invasive medical procedure. The apparatus comprises: a reference means; a processing means in communication with the ultrasonographic system; and a mounting means for mounting the reference means in a predetermined relationship to an ultrasonographic transducer. The reference means includes a plurality of apertures arranged in an predefined manner which are sized to permit at least one medical instrument to pass therethrough. The processing means determines the spatial relationship between the target tissue and the reference means and further merges a representation of the plurality of apertures with the ultrasonographic image to form a positioning image. The positioning image assists in the guiding and placement of the at least one medical instrument into a target location by identifying a path to the target location via a selected aperture. Preferably, each aperture is provided with an internal adjustment means to permit minor adjustment to the selected path.

22 Claims, 4 Drawing Sheets

APPARATUS FOR GUIDING MEDICAL INSTRUMENTS DURING ULTRASONOGRAPHIC IMAGING

This application claim benefit to provisional application Ser. No. 60/032,058 Nov. 29, 1996.

FIELD OF THE INVENTION

The present invention relates to percutaneous medical procedures and more specifically, to a method and apparatus for facilitating the guidance of medical instruments when utilizing ultrasonographic or other imaging techniques.

BACKGROUND OF THE INVENTION

One of the most important functions of clinical surgery is the resection and removal of undesirable tissues. During conventional resection surgery, the practitioner targets the undesirable tissue and using visual and tactile control, manually resects and removes that tissue. Resection implies that an incision is made in the skin to visually expose and gain access to the undesirable tissue. Not surprisingly, resection surgery usually results in considerable trauma to the patient. Until recently however, resection surgery was a generally preferred method of operating because the practitioner had confidence in the effectiveness of the procedure. This preference was primarily due to the fact that resection surgery led to, in most cases, complete removal of the undesirable tissue from the patient.

Minimally invasive surgery is an alternative surgical technique in which undesirable tissue is destroyed without necessitating resection and removal of the undesirable tissue. Minimally invasive surgical procedures can be performed using one of several known surgical techniques, the selection of which is usually determined by the type and extent of tissue to be destroyed and the location of the tissue. For example, prostate carcinoma is a common type of cancer which may be treated by using a percutaneous cryosurgical technique (a hypothermia application) in which the destruction of the tumour is accomplished by freezing.

In modern cryosurgical procedures, at least one cryoprobe having the general appearance and size of a conventional knitting needle is inserted into an undesirable tissue which is to be destroyed. The cryoprobe is provided with cooling sites typically located at the tip of the probe and cryobalation is performed by employing one of a variety of possible cooling means. Examples of such cooling means include: boiling of refrigerants; cooling of refrigerants; Joule-Thomson effects, etc. During the cryosurgical procedure, only a few small punctures are made through the skin of the patient where the cryoprobes are inserted. As is apparent from the foregoing discussion, a main objective of minimally invasive surgery such as cryosurgery is to minimize surgical trauma.

Other known surgical procedures which may be performed in a minimally invasive manner include hyperthermia, biopsy, alcohol ablation, and radiation seed implantation, photodynamic therapy and brachytherapy.

Minimally invasive surgical procedures have been shown to be effective for percutaneous contrast media injection and aspiration biopsy. Typical uses of this type of procedure include: ultrasonic Percutaneous Transhepatic Cholangiography (ultrasonic PTC) for suspected carcinoma of the bile ducts; ultrasonic Percutaneous Pancreatic Ductography (ultrasonic PPD) for suspected carcinoma of the pancreas; and ultrasonic Percutaneous Transhepatic Portography (ultrasonic PTP) for obstructing lesions of the portal vein. Other types of ultrasonographic aspiration biopsy of small intra-abdominal masses are well known and their uses have been extended to biopsy of the thyroid and breast.

One of the primary disadvantages of performing these types of procedures is that the practitioner is required to accurately guess the depth of the needle placement in the patient's body. Typically, the practitioner knows when the target tissue has been reached by the passage of a body fluid such as bile, pancreatic fluid or blood through the needle. However, the depth of penetration through the tissue is not known nor is the position and size of the suspected lesion. As will be apparent, it is important that the tissue which is the focus of the biopsy is carefully located such that the needle does not puncture other non-target organs such as the gallbladder, aorta or spleen. Unfortunately, in many situations, the visual quality of two-dimensional ultrasonography does not represent these vital structures clearly enough, especially when they are positioned behind the target tissue.

Guidance during minimally invasive procedures, and in particular, percutaneous procedures, refers to the ability to assist the practitioner during planning of the insertion points, target locations, and instrument trajectory.

Using conventional minimally invasive surgical techniques and instrumentation, imaging and guidance of instruments such as needles, probes and the like is very limited. Accordingly, the effective use of such instruments for these types of procedures requires an unusually high degree of practitioner skill. Two-dimensional imaging of the tissue is limited by virtue of the fact that only a single plane is in view at any one time and the plane of the view may be at the wrong orientation to properly image the procedure. Further, the required orientation of the two-dimensional image to guide instruments from an insertion point to a destination point may be impossible to achieve. This problem typically results from the inability to place the ultrasonographic transducer at the proper location due to factors such as patient position or bodily obstructions such as bone.

One of the most serious drawbacks of conventional techniques and instrumentation is the limited success rate and complications which can occur due to lack of practitioner skill and the significant level of guess work which typically accompanies such procedures. This can be attributed primarily to the lack of adequate imaging and instrument guidance indicated above. By way of example, in the past, when using procedures such as hypothermia, hyperthermia, and alcohol ablation, the practitioner has had to estimate the placement of the instruments and make an educated guess as to when to terminate treatment of the tissue. The educated guess approach when determining medical instrument placement, verification of placement and subsequently when to terminate treatment, primarily arises due to the inability to properly image and guide instrument placement in the tissue. The consequences of such guess work can be detrimental to the patient's health. For example, in the case of the cryosurgical prostatectomy procedure, the prostate is situated in close proximity to the rectal sphincter muscle, colon, urethra and bladder. Over freezing of the tumour into these regions may cause irreversible damage to these proximal organs, resulting in, for example, incontinence and impotence.

The above described disadvantages of minimally invasive surgical procedures were severe enough to make their use questionable for many years. However, recent improvement in two-dimensional and three-dimensional ultrasonography technology has resulted in improved resolution of the target image so that the extent of the affected tissue and efficacy of the treatment is more easily seen.

While the use of ultrasonography imaging has permitted visualization during a percutaneous medical procedure, the practitioner still experiences difficulties inserting and guiding medical instruments percutaneously to a selected target tissue. It is typically very difficult to maintain a constant trajectory to a target tissue and accordingly, during insertion, medical instrument often drift off course.

DE A 4010573 discloses a needle guide for carrying out ultrasound with an ultrasound probe. The needle guide comprises a flat plate of uniform thickness which has cylindrical openings provided in a grid pattern. The openings are provided for the guidance of puncture needles and therefore have a diameter which corresponds to the diameter of the puncture needles. The openings are conical in shape at the end which receives the puncture needle. The needle guide also has a mounting portion provided to receive an ultrasound probe. However, this needle guide assembly is deficient in that it does not permit precise control and positioning of a medical instrument.

Accordingly, there has been a long standing need for an apparatus to assist in guiding medical instruments percutaneously to a target tissue which overcomes at least one of the above-described disadvantages of conventional minimally invasive surgical procedures.

SUMMARY OF THE INVENTION

It is an object of the present invention to provide a novel apparatus for assisting instrument guidance and placement during a minimally invasive surgical procedure which obviates or mitigates at least one of the disadvantages of the previously described methods.

According to one aspect of the present invention there is provided an apparatus, employed in combination with an ultrasonographic system, for facilitating the placement of at least one medical instrument into target tissue, comprising:

a reference means including a plurality of apertures arranged in a predefined manner and sized to permit a medical instrument to pass therethrough, wherein each aperture is provided with an internal adjustment means which permits placement of the medical instrument as well as simultaneously permitting movement of the medical instrument in a perpendicular plane to a face plane of the reference means;

a mounting means for mounting the reference means in a predetermined relationship to an ultrasonographic transducer;

a processing means for determining the spatial relationship between an ultrasonographic image of the target tissue generated via the ultrasonographic transducer and the reference means, a processing means for determining the spatial relationship between an ultrasonographic image of the target tissue generated via the ultrasonographic transducer and the reference means, wherein the processing means merges a representation of the plurality of apertures in the reference means with the ultrasonographic image to assist in the placement of the at least one medical instrument in the target tissue via a selected aperture in the reference means Preferably, in accordance with the apparatus of the present invention, the predefined manner of arranging the plurality of apertures forms a Cartesian coordinate grid. Alternatively, the predefined manner of arranging the plurality of apertures is a Polar coordinate grid.

Also preferably, in accordance with the apparatus of the present invention, the plurality of apertures are provided with an index marking scheme to assist in the identification of placement coordinates and the selected aperture.

Also preferably, in accordance with the apparatus of the present invention, the mounting means includes a transverse adjustment means for adjusting the reference means transversely relative to a long axis passing through the ultrasonographic transducer.

Preferably, each aperture in the reference means comprises an internal adjustment means comprises a ball disposed in a complementary socket, generally at a mid-portion of the aperture, the ball including a passage therethrough sized to receive the at least one medical instrument therethrough and registerable with the aperture and, an axle oriented parallel to a front face of the reference means, in a plane passing through the passage, wherein the ball permits transverse adjustment of the medical instrument in a plane orthogonal to the front face.

In accordance with a second aspect, the present invention provides a method employing an ultrasonographic system for facilitating the guidance and placement of at least one medical instrument in a target tissue, comprising the steps of:

i) positioning a reference means relative to a ultrasonographic transducer in a region proximal a site on a patient which facilitates access to the target tissue;

ii) referencing the reference means to the ultrasonographic system to determine the spatial relationship therebetween;

iii) obtaining an ultrasonographic image of the target tissue;

iv) via a processing means, generating a positioning image by superimposing an image of the reference means over the image;

v) from the positioning image, selecting a target location within the target tissue where the at least one medical instrument is to be placed; and vi) from the positioning image, determining an insertion path to the target location and determining placement coordinates on the reference means.

The method may also include a step of placing the at least one medical instrument into the target tissue via the placement coordinates on the reference means, along the insertion path to the target location.

In accordance with another aspect, the present invention provides a reference means for facilitating the placement of at least one medical instrument into a target tissue, the reference means comprising:

a reference means including a plurality of apertures arranged in a predefined manner and sized to permit a medical instrument to pass therethrough, wherein each aperture is provided with an internal adjustment means which permits placement of the medical instrument as well as simultaneously permitting movement of the medical instrument in a perpendicular plane to a face plane of the reference means;

mounting means for mounting the guidance plate in a predetermined relationship to an ultrasonographic transducer; and interface means to link the guidance plate with a processing means operable to determining the spatial relationship between an ultrasonographic image of the target tissue generated by the ultrasonographic transducer and the reference means.

BRIEF DESCRIPTION OF THE DRAWINGS

A presently preferred embodiment of the present invention will now be described, by way of example only, with reference to the accompanying drawings, in which.

DETAILED DESCRIPTION OF THE PREFERRED EMBODIMENT

Figure 1:
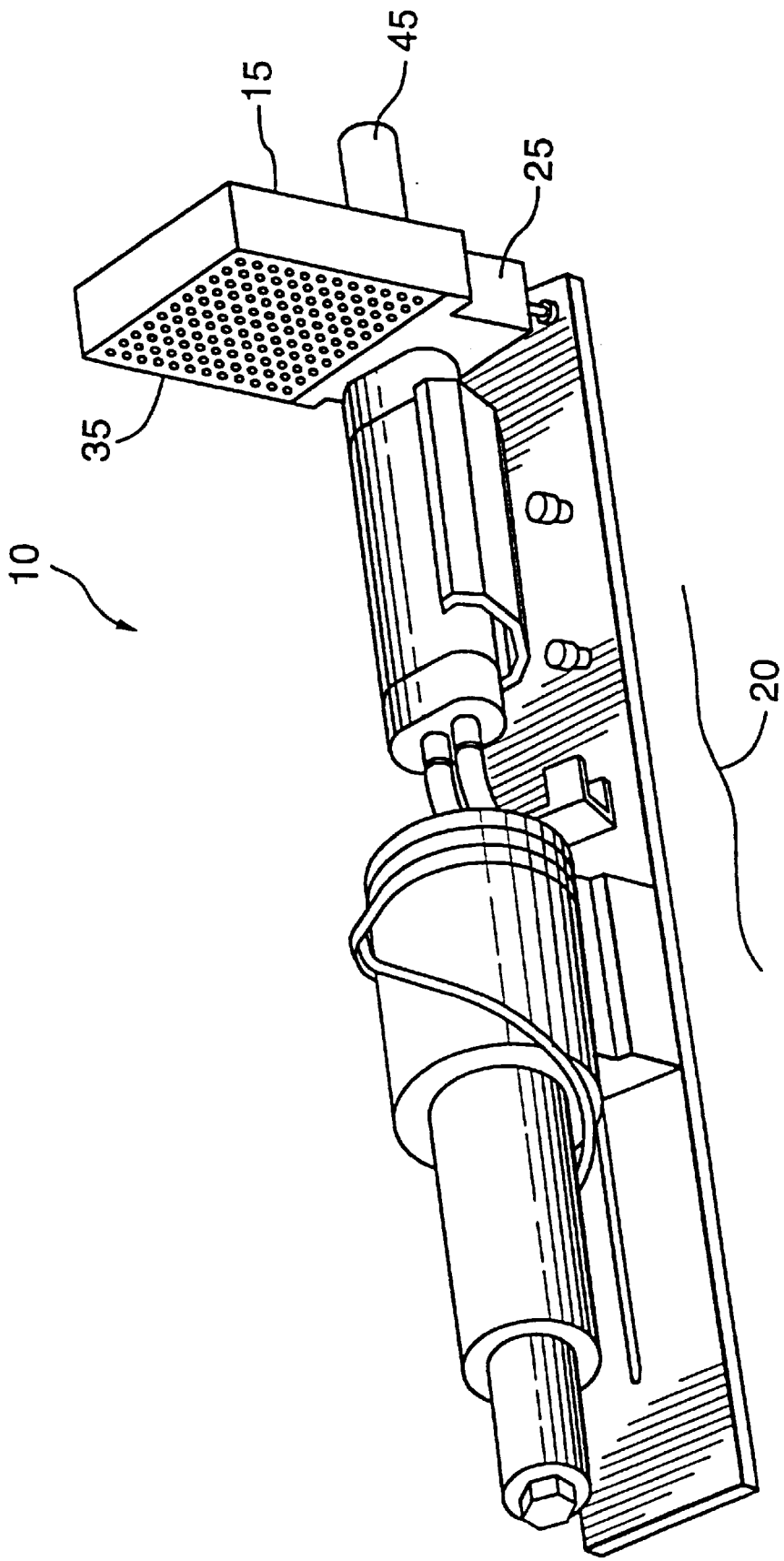
FIG. 1 shows a perspective representation of a medical instrument guidance apparatus in accordance with one embodiment of the present invention.

An apparatus for facilitating the placement of a medical instrument into a target tissue is accordance with one embodiment of the present invention is shown generally at 10 in FIG. 1. Apparatus 10 generally comprises a reference means, which in the present embodiment is in the form of a reference plate 15, movably attached to an ultrasound assembly 20 via a mounting means 25. A suitable ultrasound assembly 20 has been described in detail in U.S. Pat. No. 5,454,371, the contents of which are herein incorporated by reference, and accordingly, will not be described herein.

Figure 2:
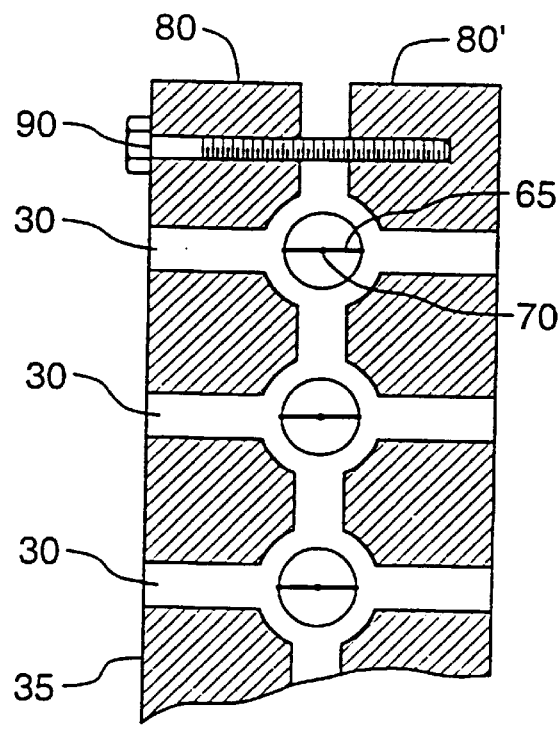
FIG. 2 shows a partial side elevation view section through a reference plate in accordance with the embodiment of FIG. 1.
Figure 3:
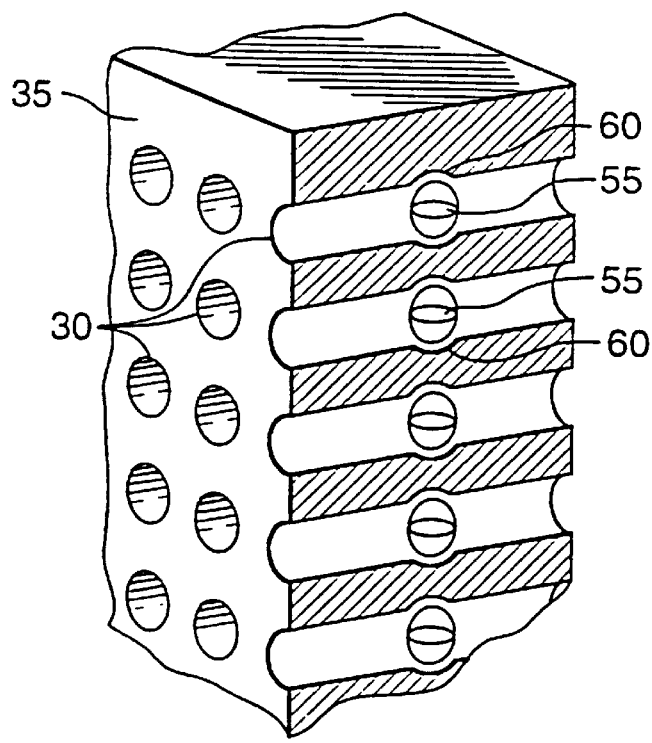
FIG. 3 is a partial perspective view of an elevation section view through a mid-section of the reference plate.
Figure 5:
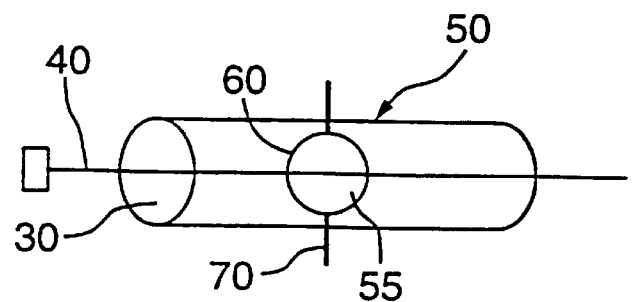
FIG. 5 is a cut-away perspective plan view of the aperture with a medical instrument inserted therein.
Figure 6:
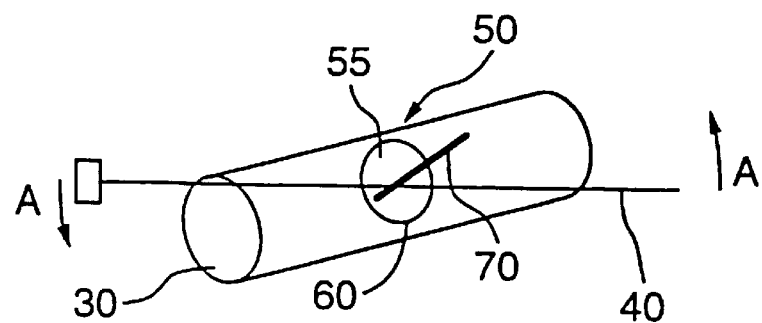
FIG. 6 is a cut-away perspective elevation view of the aperture with a medical instrument inserted therein and transversely adjusted.

As shown in FIGS. 2 and 3, reference plate 15 is provided with a plurality of regularly spaced apertures 30 in the form of a Cartesian grid. The plurality of apertures 30 pass through reference plate 15 orthogonal to a face plane 35. As shown in FIGS. 5 and 6, apertures 30 are sized to allow at least one medical instruments, such as a biopsy needle 40, to pass therethrough.

The Cartesian grid formed by apertures 30 may be provided with an indexing means (not shown) which facilitates the practitioner in the placement of biopsy needle 40. Typically, the indexing means is in the form of alphanumeric markings on face plane 35 indicating the rows and columns of apertures forming the Cartesian grid. It is contemplated that the Cartesian grid of apertures 30 could be replaced with a Polar coordinate grid structure and achieve similar results. In this case, the indexing means would be altered to indicate radius and degrees.

Figure 7:
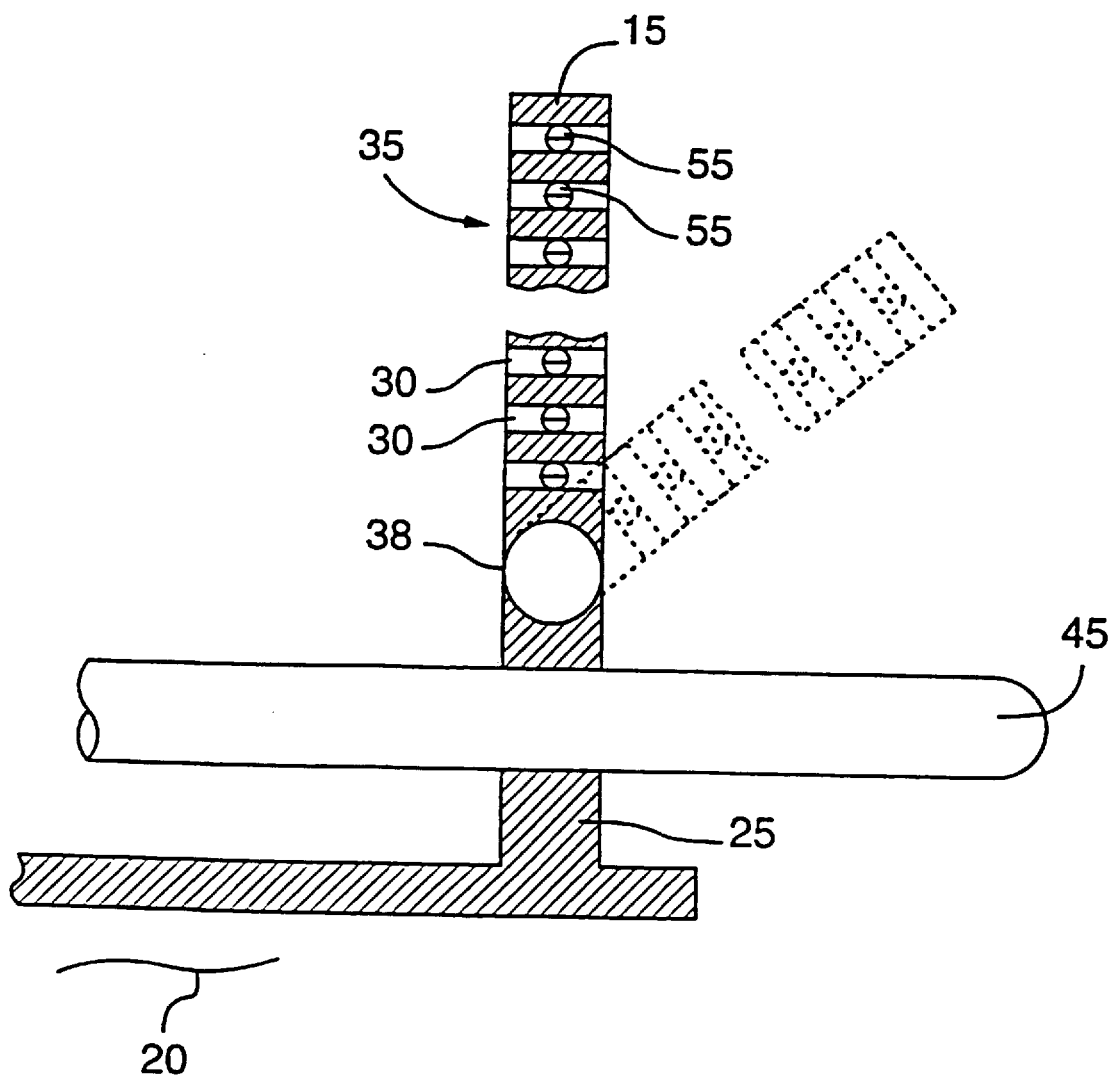
FIG. 7 is a partial side elevation view section through a portion of an instrument guidance apparatus in accordance with the embodiment of FIG. 1.

Mounting means 25 is preferably fixedly attached to a portion of ultrasound assembly 20 so as to establish a reference location between ultrasound transducer 45 of assembly 20 and reference plate 15. Mounting means 25 preferably includes an adjustment means, such as hinge 38, such that face plane 35 can be adjusted transversely with respect to the longitudinal axis of transducer 45. Reference plate 15 is shown in an alternative position with respect to ultrasound transducer 45 in dashed line in FIG. 7. The adjustment of face plane 35 with respect to transducer 45 facilitates the projection of at least a portion of the Cartesian grid of apertures 30 to be mapped onto the target location. Also preferably, reference plate 15 is moveable along the length of transducer 45. This movement may be achieved by movement of the transducer relative to a stationary plate and/or movement of the plate relative to a stationary transducer.

It is contemplated that a plurality of orientation sensors (not shown) may be included on mounting means 25. These sensors measure the orientation of face plane 35 in the X, Y, and Z planes with respect to the longitudinal axis of transducer 45. The orientation sensors may be connected to a computer to provide improved feedback to the practitioner during the preplanning for the needle placement.

Figure 4:
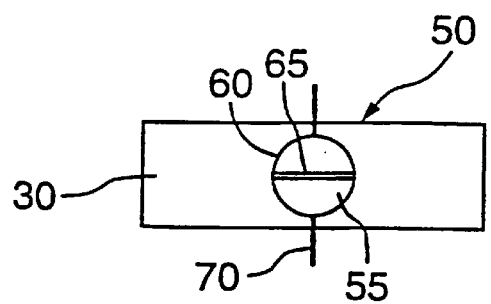
FIG. 4 is a cut-away sectional plan view of an aperture disposed through the reference plate.

To further facilitate placement of biopsy needle 40, each of apertures 30 is preferably provided with an internal adjustment means 50. As most clearly shown in FIGS. 4, 5 and 6, internal adjustment means 50 comprises a ball 55 disposed within a complementary socket 60. Socket 60 is located at a mid-point along the length of aperture 30. Each ball 55 has a passageway 65 therethrough sized to receive a portion of biopsy needle 40. Passageway 40 forms a part of aperture 30. Each ball 55 is rotatable around an axle 70 which is parallel to face plane 35. When biopsy needle 40 is received within passageway 65, rotation of ball 55 around axle 70 permits movement of the needle in a plane perpendicular to face plane 35, as shown by Arrow A in FIG. 6.

As shown in FIG. 2, for ease of construction, reference plate 15 may be formed from two face-to-face plates 80 and 80' held together by a fastener such as bolt 90. The face-to-face construction facilitates placement of balls 55 in sockets 60.

In a presently preferred embodiment, apertures 30 are approximately 10 mm long and have a diameter of about 4.75 mm. A 6 mm diameter ball 55 is placed centrally in each aperture. Passageway 65 through each ball 55 has a diameter of approximately 2 mm. With such an arrangement, the internal adjustment means provides approximately a 30° range of movement for a medical instrument (i.e., ±15° from the longitudinal axis of the aperture). If the diameter of the ball is increased to 8 mm and the diameter of the aperture is increased to 6.85 mm, then the internal adjustment means provides approximately a 50° range of movement (i.e., ±25° from the longitudinal axis of the aperture).

The operation of the reference plate will be described with reference to the use of a three-dimensional ultrasound transducer, although, as will be apparent, the reference plate is equally applicable for use with two-dimensional ultrasound. Once transducer 45 has been placed in the patient, the apparatus is initialized so that the orientation of face plane 35 and a specific reference aperture (not identified in the Figures) on Cartesian grid is referenced to transducer 45. A three-dimensional image of the target tissue is then displayed on a computer monitor and a digital image representation of the Cartesian coordinate grid is superimposed over the three-dimensional image such that the Cartesian grid of apertures 30 corresponds spacially with the imaged region.

The practitioner then determines the desired target location for the biopsy needle 40 and inputs this information to the user interface of the computer apparatus controlling ultrasound apparatus 20. Ultrasound apparatus 20 then calculates the optimal trajectory of insertion in three dimensions via an appropriate aperture 30 in reference plate 15. The results of this calculation are communicated to the practitioner through one of several possible means. Typically the results are displayed on a computer monitor by highlighting or changing the colour of the selected aperture on the positioning image or by display the appropriate index coordinates.

If the calculated trajectory of biopsy needle 40 to the target tissue is at an oblique angle to face plane 35, reference plate 15 may be moved, possibly under the guidance of the previously described orientation sensors, such that the orientation of face plane 35 is perpendicular to the calculated trajectory path.

If more than one medical instrument is required for insertion into the target tissue, the foregoing steps may be consecutively repeated for each instrument or, the plurality of target locations may be entered as a single step.

When the at least one biopsy needle 40 is inserted into the patient through the indicated aperture, the trajectory of the needle can be monitored using real-time three-dimensional ultrasonographic imaging, as described in U.S. Pat. No. 5,454,371, incorporated herein by reference. As will be apparent, the calculated trajectory of biopsy needle 40 can be superimposed over the real-time image to further assist the practitioner.

Internal adjustment means 50 provides the practitioner with the ability to make minor adjustments to the trajectory of the instrument during placement. This is particularly useful if the instrument contacts an impenetrable mass such as bone or delicate tissue such as nerves or blood vessels. The minor adjustment also provides for slight movement of the target tissue within the body which ma occur as a result of the patient's breathing. The limited movement of the internal adjustment means within the chosen aperture helps ensure that the instrument does not deviate significantly from the preferred trajectory.

While three-dimensional ultrasonographic images are preferred for viewing placement of the instruments, other imaging modalities may be employed with equal success. The three-dimensional ultrasonographic system presently employed is that disclosed in U.S. Pat. No. 5,454,371, the contents of which are herein incorporated by reference. However as will be understood by those of skill in the art, other three-dimensional ultrasonographic systems may be employed with the apparatus and method of the present invention with equal success.

In is further contemplated that three-dimensional reconstruction of other imaging modalities such as Computer Tomography (CT) or Magnetic Resonance Imaging (MRI) can be used in addition to, or as a replacement for, the three-dimensional ultrasonographic model. In this embodiment ultrasonographic transducer 45 is manoeuvred until a real-time two-dimensional ultrasonographic image is produced of a plane showing characteristic landmarks of the organ anatomy or the target tissue. This plane is then found in a three-dimensional model generated using the CT or MRI modalities and an image is generated. When the two-dimensional real-time ultrasonographic image matches that of the three-dimensional model image, the characteristic pixels are designated. These reference pixels can again be tracked on a computer to allow reorientation of the three-dimensional MRI or CT model to the new organ position.

Although the present invention has been described with reference to the placement of a biopsy needle, it is envisioned that the apparatus may be readily adapted to may other medical instruments, such as cryosurgical probes, guidance sheathes, thermocouples an the like. Further, the present invention is not limited to use in cryosurgery. It is envisioned that the instrument guidance techniques disclosed herein are equally applicable to other non-invasive surgical techniques such as hyperthermia, alcohol ablation, radiation seed implantation, photodynamic therap and brachytherapy.

The present invention has been described with reference to a presently preferred embodiment. Other variations and embodiments of the present invention may be apparent to those of ordinary skill in the art. Accordingly, the scope of protection sought for the present invention is only limited as set out in the attached claims.

What is claimed is:

1. An apparatus, employed in combination with an ultrasonographic system, for facilitating the placement of at least one medical instrument into target tissue, comprising:

a reference means including a plurality of apertures arranged in a predefined manner and sized to permit a medical instrument to pass therethrough, wherein each aperture is provided with an internal adjustment means which permits placement of the medical instrument as well as simultaneously permitting movement of the medical instrument in a perpendicular plane to a face plane of the reference means;

a mounting means for mounting the reference means in a predetermined relationship to an ultrasonographic transducer;

a processing means for determining the spatial relationship between an ultrasonographic image of the target tissue generated via the ultrasonographic transducer and the reference means;

wherein the processing means merges a representation of the plurality of apertures in the reference means with the ultrasonographic image to assist in the placement of the at least one medical instrument in the target tissue via a selected aperture in the reference means.

2. An apparatus according to claim 1, wherein the internal adjustment means comprises a ball disposed in a complementary socket, the ball moveable within the socket and including a passage therethrough sized to receive the at least one medical instrument therethrough and registerable with the aperture.

3. An apparatus according to claim 2, wherein the ball is located generally at a mid portion of the aperture.

4. An apparatus according to claim 3, wherein the ball is moveably mounted on an axle oriented parallel to a front face of the reference means, in a plane passing through the passage, wherein the ball permits movement of the medical instrument in a plane perpendicular to the front face of the reference means.

5. An apparatus according to claim 1, wherein the predefined manner of arranging the plurality of apertures forms a Cartesian coordinate grid.

6. An apparatus according to claim 1, wherein the mounting means is attached between the ultrasonographic transducer and the reference means.

7. An apparatus according to claim 1, wherein the reference means comprises a generally rectangular plate.

8. An apparatus according to claim 7, wherein one face of the rectangular plate is shaped to fit the contours of a portion of a human body.

9. An apparatus according to claim 1, wherein the plurality of apertures are provided with an index marking scheme to assist in the identification of placement coordinates and the selected aperture.

10. An apparatus according to claim 1, wherein the mounting means includes a transverse adjustment means for adjusting the reference means transversely relative to a long axis passing through the ultrasonographic transducer.

11. An apparatus according to claim 1, wherein the ultrasonographic system is a three-dimensional ultrasonographic system.

12. A method employing an ultrasonographic system for facilitating the guidance and placement of at least one medical instrument in a target tissue, comprising the steps of:

i) positioning a reference means relative to a ultrasonographic transducer in a region proximal a site on a patient which facilitates access to the target tissue;

ii) referencing the reference means to the ultrasonographic system to determine the spatial relationship therebetween;

iii) obtaining an ultrasonographic image of the target tissue;

iv) via a processing means, generating a positioning image by superimposing an image of the reference means over the ultrasonographic image;

v) from the positioning image, selecting a target location within the target tissue where the at least one medical instrument is to be placed; and vi) from the positioning image, determining an insertion path to the target location and determining placement coordinates on the reference means.

13. The method according to claim 12, wherein the ultrasonographic system is a three-dimensional ultrasonographic system.

14. The method according to claim 13 wherein the method includes a further step, concurrent with step viii), of monitoring placement of the at least one medical instrument along the insertion path to the target location, via the placement coordinates, with one or more images generated by the three-dimensional ultrasonographic system.

15. The method according to claim 12, further comprising a step of placing the at least one medical instrument into the target tissue via the placement coordinates on the reference means, along the insertion path to the target location.

16. The method according to claim 12 wherein, steps i) through vii) are repeated for a plurality of medical instruments.

17. A reference means for facilitating the placement of at least one medical instrument into a target tissue, the reference means comprising:

a reference means including a plurality of apertures arranged in a predefined manner and sized to permit a medical instrument to pass therethrough, wherein each aperture is provided with an internal adjustment means which permits placement of the medical instrument as well as simultaneously permitting movement of the medical instrument in a perpendicular plane to a face plane of the reference means;

mounting means for mounting the guidance plate in a predetermined relationship to an ultrasonographic transducer; and interface means to link the guidance plate with a processing means operable to determining the spatial relationship between an ultrasonographic image of the target tissue generated by the ultrasonographic transducer and the reference means.

18. A reference means according to claim 17, wherein the internal adjustment means comprises a ball disposed in a complementary socket, the ball moveable within the socket and including a passage therethrough and registerable with the aperture.

19. A reference means according to claim 18, wherein the ball is located generally at a mid portion of the aperture.

20. A reference means according to claim 18, wherein the ball is moveably mounted on an axle oriented parallel to a front face of the reference means, in a plane passing through the passage, wherein the ball permits movement of the medical instrument in a plane perpendicular to the front face of the reference means.

21. A reference means according to claim 17, wherein the predefined manner of arranging the plurality of apertures forms a Cartesian coordinate grid.

22. A reference means according to claim 17, wherein the ultrasonograph transducer is a three-dimensional ultrasonographic transducer.

* * * * *